United States Patent [19]

Ohta et al.

[11] Patent Number: 5,265,169
[45] Date of Patent: Nov. 23, 1993

[54] METHOD OF DISCRIMINATING PARTICLE AGGREGATION PATTERN

[75] Inventors: Masato Ohta; Yasuhiko Yokomori; Toshiyuki Furuta, all of Shizuoka, Japan

[73] Assignee: Suzuki Motor Corporation, Shizuoka, Japan

[21] Appl. No.: 775,809

[22] Filed: Oct. 11, 1991

[30] Foreign Application Priority Data

Oct. 31, 1990 [JP] Japan .................................. 2-294123

[51] Int. Cl.$^5$ .............................................. G06K 9/00
[52] U.S. Cl. ................................. 382/6; 364/413.01; 356/39; 358/903
[58] Field of Search ................. 382/6, 50, 53; 364/413.01, 413.08, 413.1, 555, 525, 554; 356/39; 358/107, 903

[56] References Cited

U.S. PATENT DOCUMENTS

| | | | |
|---|---|---|---|
| 4,319,271 | 3/1982 | Hurni et al. | 358/903 |
| 4,448,534 | 5/1984 | Wertz et al. | 356/435 |
| 4,563,430 | 1/1986 | Kano et al. | 436/164 |
| 4,580,895 | 4/1986 | Patel | 356/39 |
| 4,794,450 | 12/1988 | Saito et al. | 364/413.01 |
| 5,096,835 | 3/1992 | Yokomori et al. | 356/39 |

FOREIGN PATENT DOCUMENTS

58-102157 6/1983 Japan .
2-116735 1/1990 Japan .

*Primary Examiner*—Jose L. Couso
*Attorney, Agent, or Firm*—Flynn, Thiel, Boutell & Tanis

[57] ABSTRACT

A method for identifying the presence or absence of an aggregation of particles distributed on a translucent surface includes the steps of providing a light sensing device for sensing light incident thereon and producing an output value which represents the intensity of the incident light, and identifying a first output value which is produced by the light sensing device when there is no light incident thereon. The method also identifies a second output value which is produced by the light sensing means when, with no particles present on the translucent surface, light is directed through the translucent surface onto the light sensing device. With a distribution of particles deposited on the translucent surface, light is directed through the translucent surface and onto the light sensing device, causing the light sensing device to produce a third output value. A final output value is then determined as a function of said first, second and third output values.

8 Claims, 7 Drawing Sheets

FIG. 1

20 (AGGREGATION REACTION DETECTING APPARATUS)

(BEFORE SHADING)

FIG. 8(b)

(AFTER SHADING)

FIG. 12 PRIOR ART
(CROSS SECTIONAL PLANE AT THRESHOLD LEVEL)

SOLID LINE : AREA DATA

METHOD OF DISCRIMINATING PARTICLE AGGREGATION PATTERN

CROSS REFERENCE TO RELATED APPLICATIONS

This application is related to copending U.S. Ser. Nos. 07/520 093 (filed May 7, 1990), now U.S. Pat. No. 5,096,835, 07/700,568 (filed May 15, 1991) and 07/700 618 (filed May 15, 1991) now U.S. Pat. No 5,230,026. These copending applications have been assigned, at least in part, to the assignee of this application.

FIELD OF THE INVENTION

The invention relates to a method of discriminating a particle aggregation pattern and, more particularly, to a particle aggregation pattern discriminating method which is suitable for determination of various kinds of blood types from an aggregation reaction pattern of blood corpuscle particles and for detection of antigens and antibodies by what is called a microtiter method in clinical examination.

BACKGROUND OF THE INVENTION

Hitherto, in the medical field, there is widely used a method whereby aggregation patterns of blood corpuscle particles, latex particles, and carbon particles are discriminated and various components (for instance, blood type, various antibodies, various proteins, etc.) in the blood, virus, and the like are detected and analyzed. A microtiter method is relatively widely used as such an aggregation pattern discriminating method.

According to the microtiter method in the immunity measurement, the blood is aggregated on a microplate by a predetermined method and the presence or absence of the aggregation is examined or an area or the like of the aggregation pattern is calculated, thereby measuring a microquantity of immune component. Hitherto, the judgement of the presence or absence of the aggregation has been performed by the eyes. However, in recent years, automatization of such a judgement is also being developed.

The discrimination regarding the aggregation patterns is integratedly executed by a method whereby the presence or absence of aggregation is discriminated by detecting a distribution of particles in a translucent well (reaction vessel) and identifying an aggregation of particles as an area of the well whose luminance is equal to or less than a predetermined luminance level, or by comparing the particle distribution with a reference aggregation pattern or a reference non-aggregation pattern, or further by making continuous step-wise dilution series of specimen and samples, or the like.

Automatization of the discrimination of the aggregation patterns is accomplished by: optical means; and electrical arithmetic processing means for electrically arithmetically processing aggregation patterns which are obtained by the optical means.

Figure 9:
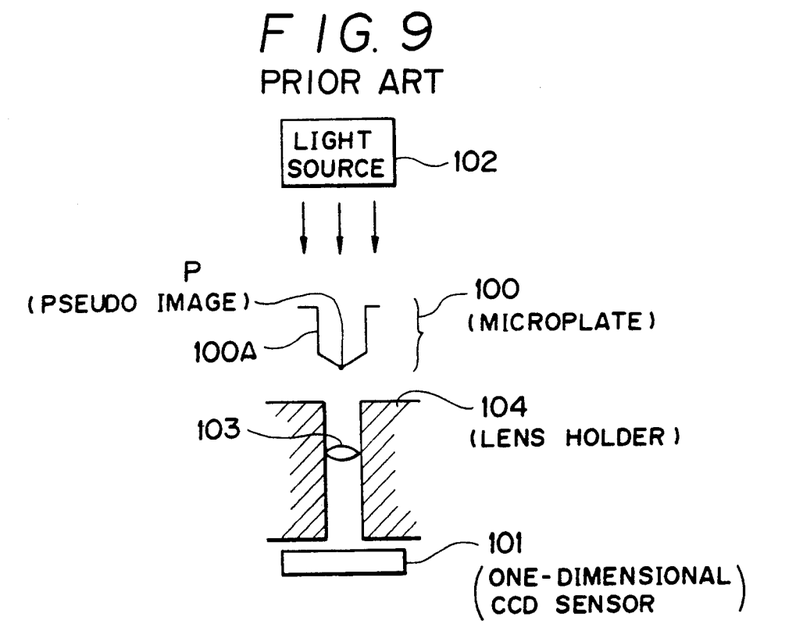
FIG. 9 is a diagram for explaining a conventional example.

FIG. 9 shows a conventional example. In the conventional example shown in FIG. 9, an aggregation pattern P of particles in a well (reaction vessel) 100A formed on a microplate 100 is optically projected onto a one-dimensional CCD (charge coupled of vice) sensor) 101. The CCD sensor 101 or the microplate 100 is relatively sequentially finely moved in the direction perpendicular to the paper surface, causing the CCD sensor to occupy a plurality of scanning positions relative to the reaction vessel, thereby enabling the one-dimensional CCD sensor to scan the pattern P many times (see FIG. 11), thus obtaining a (bright and dark) two-dimensional image of the aggregation pattern P. In FIG. 9, reference numeral 102 denotes a light source; 103 an image forming lens; and 104 a lens holder.

In the above conventional example, however, there are the following various problems.

Figure 10:
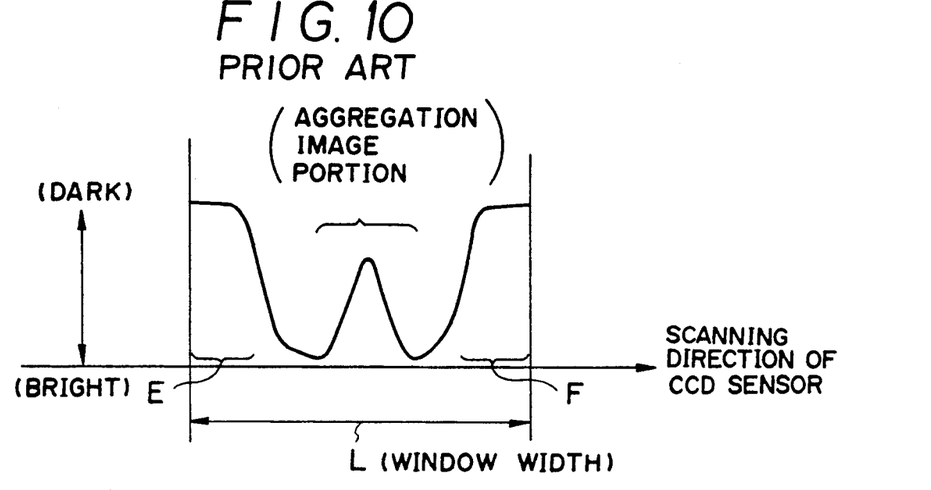
Figure 11:
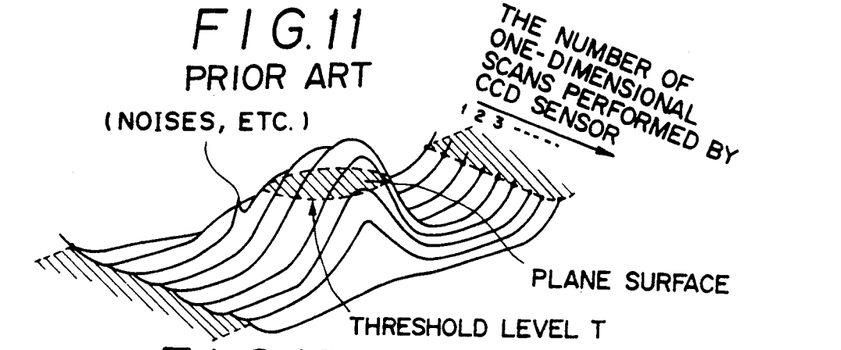
Figure 12:
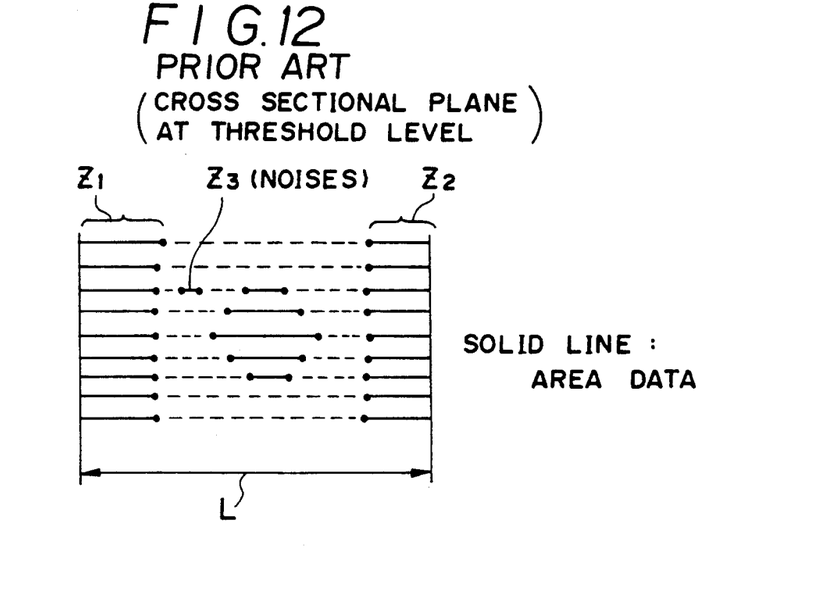

An aggregation image peripheral portion (portion other than the image) becomes dark due to influences by aberrations of the lens holder 104 and the lens 103 and the like and an output of the CCD sensor corresponding to such a peripheral portion becomes remarkably dark at both edge portions E and F of a window width L of such a portion as shown in FIG. 10. Particularly, the data obtained are collected and a solid as shown in FIG. 11 is formed. After that, the aggregation pattern is discriminated by using area data of a cross sectional plane surface which is obtained by cutting the solid at a proper threshold level T. In the case of executing such a discrimination, for instance, as shown in FIG. 12, dark portions $Z_1$, $Z_2$, and $Z_3$ are largely displayed as area data (solid line portions in the diagram) due to influences by the dark portions of the aggregation image peripheral portion, disturbance lights, and electrical noises.

Figure 13A:
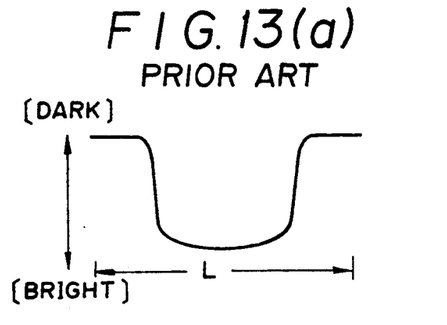
Figure 13B:
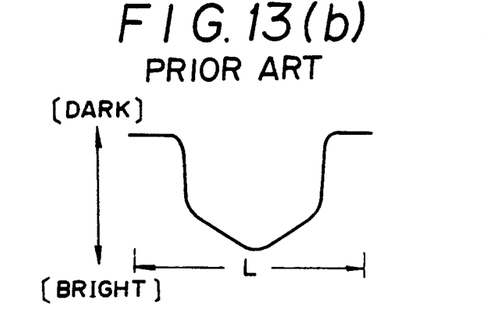
Figure 13C:
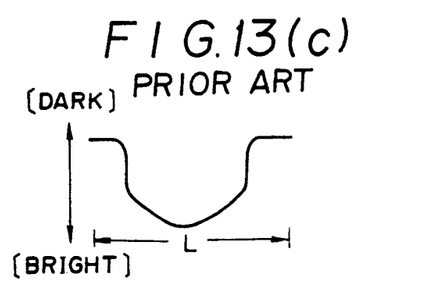

FIG. 13(a) shows an output waveform in the case where the microplate is not inserted. FIG. 13(b) shows an output waveform in the case where the microplate has been inserted. FIG. 13(c) shows an output waveform in the case where the bottom surface of the reaction vessel of the plate is cloudy due to influences by a material and a surface process. As will be obviously understood from the above diagrams, there is a case where the brightness and darkness of the light due to the shape and material of the microplate, the reaction vessel, surface process, and the like are mixed as noises into the output signal and exert an influence on the area data.

Figure 13D:
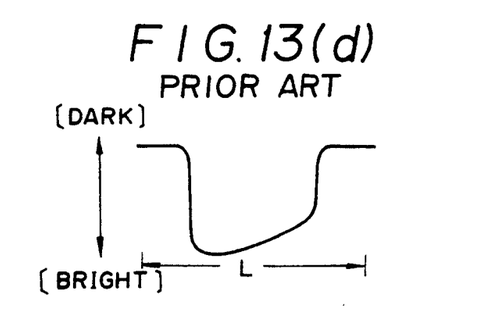

As shown in FIG. 13(d), there is also a case where the brightness and darkness of the light due to the uneven illumination exert an influence on the area data.

Figure 14A:
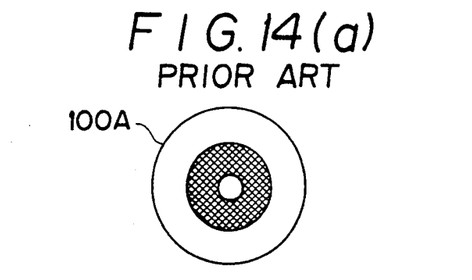
Figure 14B:
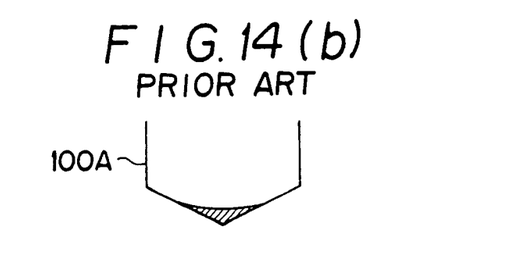
Figure 14C:
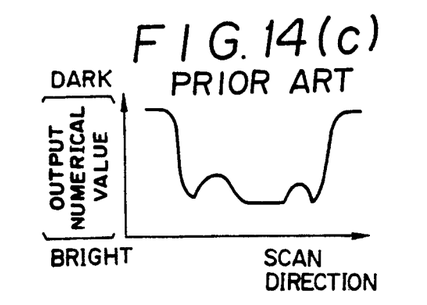
Figure 14D:
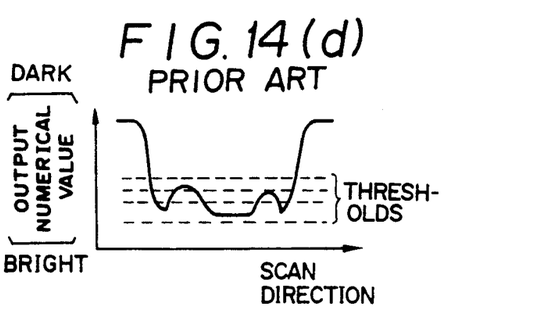

As shown in FIGS. 14(a) to 14(d), in the case of a doughnut-like image such that the aggregation image is large and the central portion is bright, the area data largely differs in dependence on the setting of the threshold level as will be obviously understood from FIG. 14(d), so that it is very difficult to accurately discriminate the aggregation pattern using area data.

It is an object of the invention to avoid the inconveniences of such a conventional example and, more particularly, to provide a particle aggregation pattern discriminating method which can fairly improve discriminating accuracy as compared with the conventional method.

The invention uses a method of discriminating a particle aggregation pattern whereby a plate for use in aggregation reaction examination and having one or two or more reaction vessels is provided, a bottom surface of each of the reaction vessels is uniformly illuminated through the plate for the aggregation reaction examination by light emitting means arranged on one side of the plate, transmitted light is received through image forming lenses by a one-dimensional photosensitive device arranged on the other side of the plate for the aggregation reaction examination, and a particle distribution is formed on the bottom surface of the reaction vessel as a result of particles precipitated from the reaction solution stored in the reaction vessel. The transmitted light provides an image of the particle distribution, which image is fetched by the photosensitive device as light reception data. An output signal of the one-dimensional photosensitive device is processed to thereby form at least one transmission luminous intensity curve, and an aggregation pattern is discriminated on the basis of the transmission luminous intensity curve in accordance with a predetermined reference, wherein transmission luminous intensity curve data representing an empty state of the reaction vessel is previously stored into a memory, the reaction solution is stored into the reaction vessel, transmission luminous intensity curve data representing a state in which the particles have precipitated after the elapse of a predetermined time is subsequently fetched, waveform data of only an aggregation image is calculated by executing predetermined arithmetic operations on the basis of the transmission luminous intensity curve data representing precipitated particles and the transmission luminous intensity curve data representing the empty vessel, and an aggregation pattern is discriminated on the basis of the calculated waveform data of only the aggregation image.

BRIEF DESCRIPTION OF THE DRAWINGS

An embodiment of the invention will be described hereinbelow on the basis of the attached drawings, in which:

FIG. 8(*a*) is a diagram showing transmission luminous intensity curve data after particle precipitation but before shading, and corresponding to a doughnut-like aggregation image;

FIG. 8(*b*) is a diagram showing the data which results when shading is applied to the data in FIG. 8(*a*);

FIGS. 10, 11, 12, 13(*a*)–(*d*) and 14(*a*)–(*d*) are diagrams for explaining problems in the conventional example.

DETAILED DESCRIPTION

Figure 1:
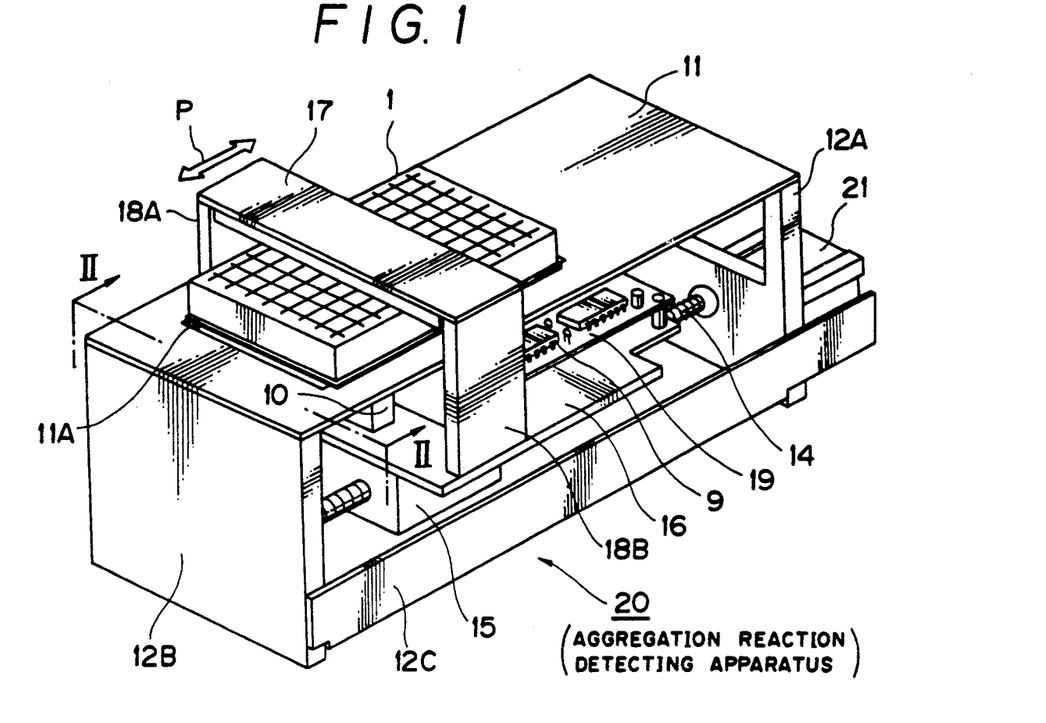
FIG. 1 is a perspective view showing an aggregation reaction detecting apparatus used for performing a particle aggregation pattern discriminating method of the invention.

FIG. 1 shows an example of an apparatus for use in a particle aggregation pattern discriminating method according to the invention.

Figure 3:
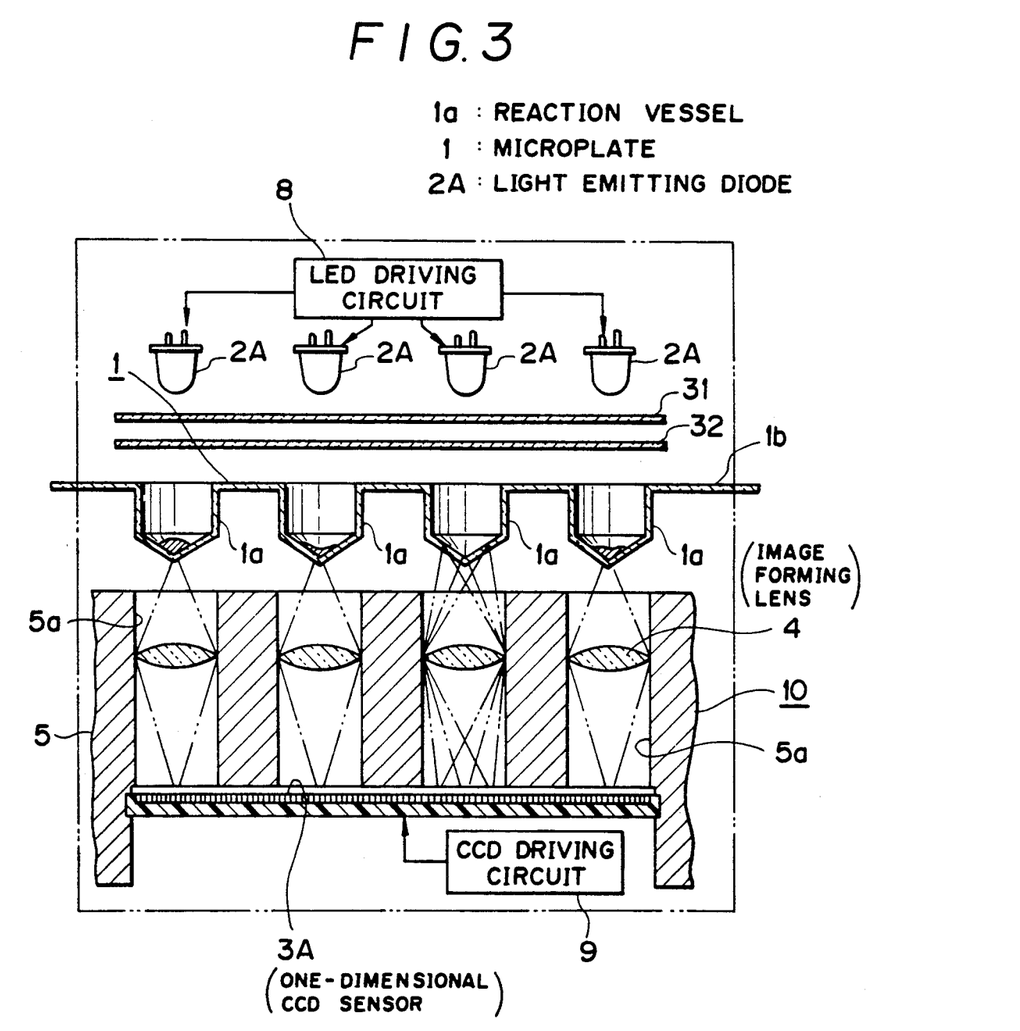
FIG. 3 is an explanatory diagram showing the arrangement of a light emitting means, photosensitive means, and the like in the apparatus of FIG. 1.

An aggregation reaction detecting apparatus 20 shown in FIG. 1 comprises: a horizontal plate 11; and supporting members 12A and 12B to support the horizontal plate 11 from below. An opening 11A is formed in a part of the horizontal plate 11 and a microplate 1 serving as a plate for aggregation reaction examination is arranged in the opening 11A. As shown in FIG. 3, the microplate 1 includes a translucent base plate 1b in which are arranged a number of reaction vessels 1a, each of which has a bottom surface formed like a circular cone. The reaction vessels 1a are arranged and formed like a matrix. In the disclosed embodiment, a microplate in which the reaction vessels 1a are arranged in eight rows and twelve columns and formed like a matrix is used.

Figure 2:
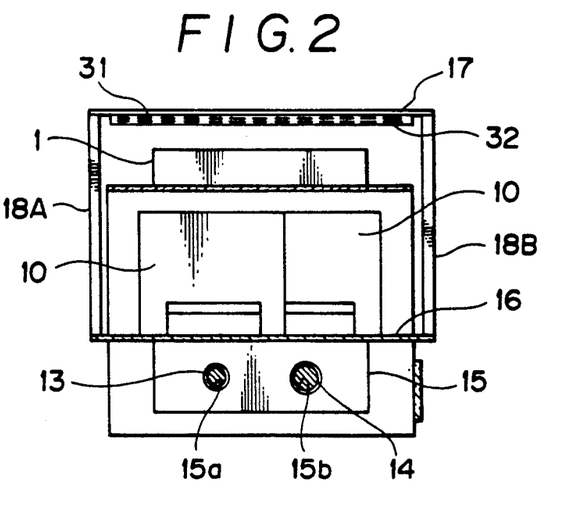
FIG. 2 is a sectional view taken along line II—II in FIG. 1.

A reinforcing plate 12C for coupling and fixing both of the supporting members 12A and 12B is attached between the supporting members 12A and 12B. A guide shaft 13 shown in FIG. 2 is attached between the supporting members 12A and 12B along a longitudinal direction of the horizontal plate 11. Further, another shaft 14 is arranged between the supporting members 12A and 12B in parallel with the guide shaft 13 and is rotatably supported. The shaft 14 is externally threaded along the whole length thereof.

A box 15 shown in FIGS. 1 and 2 is attached to both of the shafts 13 and 14 so as to be reciprocatingly movable along both of the shafts 13 and 14. A hole 15*a* having a diameter which is almost equal to a diameter of the shaft 13, and an internally threaded hole 15*b* having a diameter which is almost equal to a diameter of the shaft 14 are formed in the box 15. The box 15 is thus threaded onto the threaded shaft 14.

Figure 4:
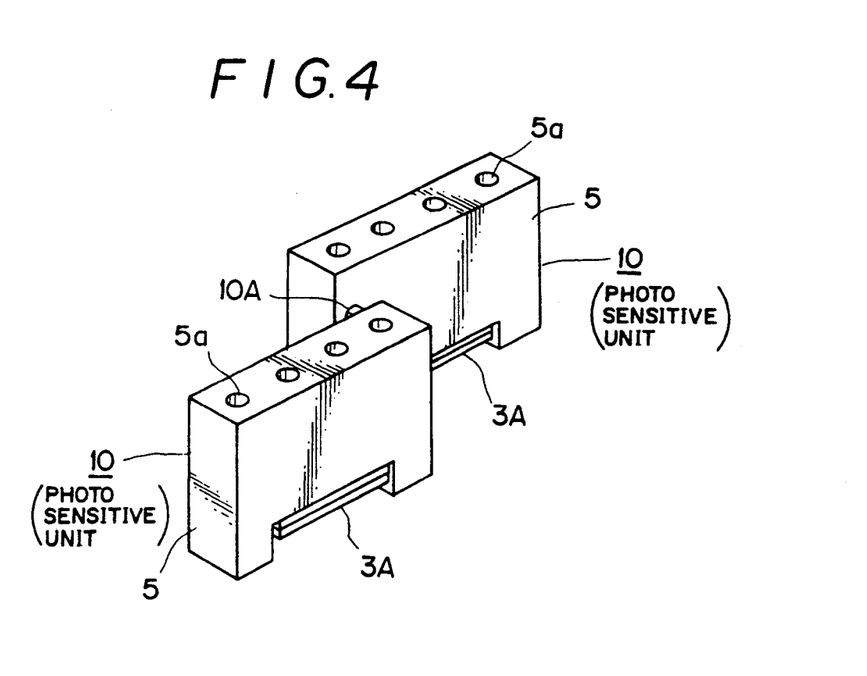
FIG. 4 is an external perspective view showing the photosensitive unit of FIG. 3.

A movable plate 16 which mounts photosensitive units 10 (shown in FIGS. 3 and 4) is arranged and fixed onto the upper surface of the box 15 in parallel with the horizontal plate 11. Light emitting diodes 2A (shown in FIG. 3) are fixed to the lower surface of an upper plate 17. Supporting plates 18A and 18B to support the upper plate 17 at both ends are fixed onto the upper surface of the movable plate 16 so as to upstand perpendicularly from the movable plate 16. Light diffusing plates 31 and 32 (shown in FIG. 3) are integratedly held to the lower surface of the upper plate 17 below the LEDs 2A. An LED driving circuit 8 (refer to FIG. 3), which is conventionally constructed by an IC or the like and is used to drive the light emitting diodes 2A, is also attached to the lower surface of the upper plate 17.

A board 19 (see FIG. 1) arranged in parallel with the movable plate 16 is fixed onto the upper surface of the movable plate 16 A CCD driving circuit 9, which is conventionally constructed by an IC or the like and is used to drive a one-dimensional CCD sensor 3A (which will be explained hereinlater), is attached onto the board 19.

Further, two photosensitive units 10, which are constructed as shown in FIG. 3, are arranged on the upper surface of the movable plate 16 such that parts of the photosensitive units, in the longitudinal direction of those units, are mutually overlapped. The units 10, in this case, are arranged to extend longitudinally along the column directions of the matrix of reaction vessels 1a arranged on the microplate 1 (i.e. left to right in FIG. 2). The overlapping photosensitive units 10 are actually coupled by a coupling member 10A shown in FIG. 4. The units 10 are offset from each other in the row direction of the reaction vessel matrix, and overlap each other in the column direction (see FIGS. 2 and 4).

As shown in FIG. 3, the photosensitive unit 10 comprises: a lens holder 5; image forming lenses 4 held by the lens holder 5; and the one-dimensional CCD sensor 3A as a one-dimensional photosensitive device attached to the bottom portion of the lens holder 5. A plurality of (four in the disclosed embodiment) holes 5a are formed in the lens holder 5 at intervals each of which is equal to a distance between adjacent reaction vessels 1a along the longitudinal direction of the lens holder. The image forming lenses 4 are fixed to the peripheral wall portion of each of the holes 5a. The foregoing one-dimensional CCD sensor 3A is held to the bottom portion of the lens holder 5 in parallel with the microplate 1 so as to be spaced downwardly by a predetermined distance from the image forming lens 4, that is, by a distance which is almost equal to the focal distance of the image forming lens 4. Each photosensitive unit 10 is fixed to the upper surface of the movable plate 16 in a manner such that, upon movement of plate 16, the four holes 5a and lenses 4 of each unit 10 register vertically with four of the reaction vessels 1a, the reaction vessels 1a vertically overlying the respective lenses 4.

The offset of the photosensitive units 10 in the row direction of the reaction vessel matrix, and the overlap of the units 10 in the column direction are such that, when one unit 10 properly registers with four reaction vessels 1a in one column, the other unit 10 properly registers with four reaction vessels 1a in an adjacent column. Also, these two sets of four reaction vessels in adjacent columns do not overlap each other in the column direction. Thus, one reaction vessel from each row is examined when the photosensitive units 10 are moved into vertical registry with the reaction vessels 1a (see FIGS. 1, 2 and 4).

In FIG. 3, the light emitting diodes 2A serving as light emitting means are arranged over the microplate 1 so as to face the image forming lenses 4. The two light diffusing plates 31 and 32 are arranged between the light emitting diodes 2A and the microplate 1 so as to be parallel with each other and spaced from each other by a predetermined interval. The light emitting diodes 2A and the light diffusing plates 31 and 32 are actually integratedly attached together with the LED driving circuit 8 to the lower surface of the upper plate 17 mentioned above.

A motor 21 (FIG. 1) to apply a rotational force to the threaded shaft 14 through a gear mechanism (not shown) is provided on the outside of the supporting member 12A. In the embodiment, therefore, when the motor 21 is driven, the threaded shaft 14 rotates to displace the box 15 so that the movable plate 16 and the upper plate 17 are integrally reciprocated in the direction of the arrow P in FIG. 1, namely, along the row direction of the matrix of reaction vessels 1a on the microplate 1. During such integral movement of the plates 16 and 17, the horizontal plate 11 and the microplate 1 are sandwiched from the upper and lower directions. That is, plate 17 passes above plates 1 and 11, and plate 16 passes below them.

The operation of the aggregation reaction detecting apparatus 20 constructed as mentioned above will now be described.

When the motor 21 is driven, the movable plate 16 starts moving and a positioning means, for example a limit switch (not shown), is monitored by a CPU, for example a conventional microprocessor circuit (not shown). When the photosensitive units 10 shown in FIG. 2 are moved to position the lenses 4 vertically below the reaction vessels 1a on the microplate 1, the lights from the light emitting diodes 2A are irradiated onto the microplate 1 through the light diffusing plates 31 and 32. The light from LEDs 2A is transmitted through the eight reaction vessels 1a (corresponding to the eight lenses) which are presently located over the photosensitive units 10, and the light is received by the one-dimensional CCD sensor 3A through the image forming lenses 4.

Output signals from the one-dimensional CCD sensor 3A are sent to the CPU via A/D converters (not shown). The CPU determines the amount of movement of the movable plate 16 from a feed amount (rotational amount) of the motor and calculates which eight reaction vessels are being examined, thereby automatically discriminating an aggregation pattern of the specimen in each reaction vessel in the following manner.

Figure 5:
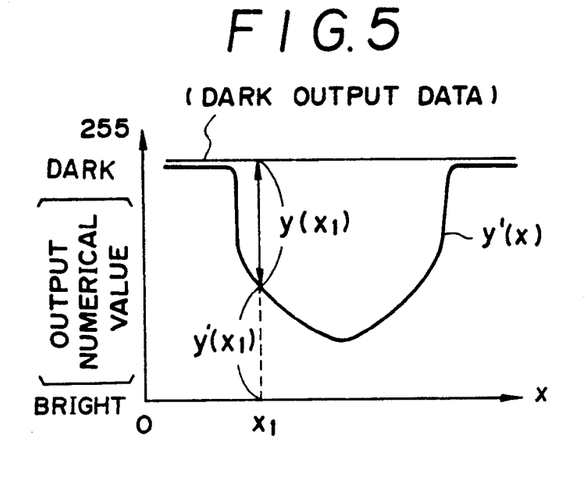
FIG. 5 is a diagram showing an example of transmission luminous intensity curve data when the reaction vessel of the microplate is empty.
Figure 6:
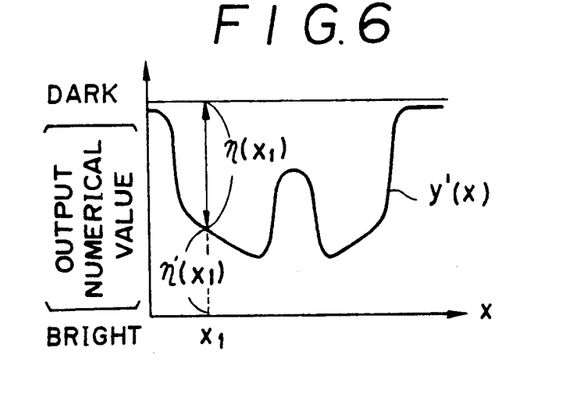
FIG. 6 is a diagram showing an example of transmission luminous intensity curve data when particles have precipitated in the reaction vessel.
Figure 7:
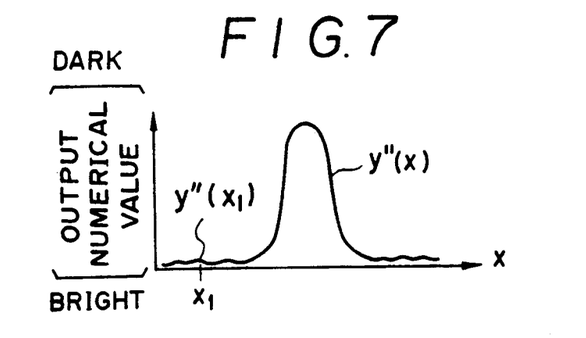
FIG. 7 is a diagram showing data of only aggregation images which are derived from the data of FIGS. 5 and 6.

A method of discriminating the particle aggregation patterns in the embodiment will now be described with reference to FIGS. 5 to 7.

(A) First, the CPU fetches transmission luminous intensity curve data when the reaction vessel 1a is empty (hereinafter referred to as "empty plate data") and stores this data into a memory thereof. The empty plate data is shown by the curve $y'(x)$ in FIG. 5. The variable x represents positions along the one-dimensional scanning direction of the CCD sensor 3A.

(B) Subsequently, CCD dark output data (i.e. the output from the CCD sensor when no light enters the CCD sensor), which has previously been stored in the memory, is used as a reference value and the above empty plate data (for example, $y'(x_1)$ in FIG. 5) is subtracted from the dark output data, thereby obtaining $y(x_1)=[\text{dark output data}]-y'(x_1)$. Thus, $y(x)=[\text{dark output data}]-y'(x)$.

(C) The maximum value 255 of the data output (in the disclosed embodiment, eight-bit data (0-255) is considered) is divided by the data $y(x_1)$ obtained as mentioned above, thereby calculating a gain function, $\text{gain}[x_1]=255/y(x_1)$. Each value of the gain function is set in correspondence to each data point of $y(x)$ one by one by repeating the above procedures (B) and (C). Thus, $\text{gain}[x]=255/y(x)$.

(D) The reaction solution is stored into the reaction vessel. When particles precipitate after the elapse of a predetermined time, the CPU fetches the transmission luminous intensity curve data ("light reception data") at that time in a manner similar to the above. This data is shown by the curve $\eta'(x)$ in FIG. 6.

(E) The CPU subsequently subtracts the relevant transmission luminous intensity curve data (for example, $\eta'(x_1)$ in FIG. 6) from the dark output data in a manner similar to the above procedure (B), thereby obtaining $\eta(x_1)=[\text{dark output data}]-\eta'(x_1)$ ("precipitated plate data"). The above calculation is executed for each data point of $\eta'(x)$ one by one. Thus, $\eta(x)=[\text{dark output data}]-\eta'(x)$.

(F) The CPU subsequently multiplies the appropriate gain value from step (C) by the corresponding value of $\eta(x)$, for example $\eta(x_1)$, thereby calculating $\eta_1(x_1)=\eta(x_1)\times\text{gain}[x_1]$. Thus, $\eta_1(x)=\eta(x)\times\text{gain}[x]$.

(G) By subtracting $\eta_1(x_1)$ from the dark output data, the final output data $$y''(x_1)=[\text{dark output data}]-\eta_1(x_1)$$

is calculated and generated. Thus, $y''(x)=[\text{dark output data}]-\eta_1(x)$.

(H) As mentioned above, waveform data $y''(x)$ of only the aggregation images ("aggregation image data38") is calculated as final output data for each scan and is used for discrimination. The waveform data $y''(x)$ of only the aggregation images is shown in FIG. 7.

(I) The waveform data y"(x) of only the aggregation images (hereinafter referred to as "data after shading") is formed for every scan of the one-dimensional CCD sensor 3A, thereby obtaining a solid which comprises the data after shading and is similar to that of FIG. 11.

(J) Finally, by cutting the solid at a predetermined threshold level similar to T in FIG. 11, a plane surface similar to the plane surface in FIG. 11 is defined by the intersection of the threshold plane and the solid. An area S of the plane surface is calculated using the well known quadrature by parts technique. The area S is compared with reference areas which have been calculated from predetermined reference patterns (a reference non-aggregation pattern and a reference aggregation pattern), thereby judging whether the aggregation pattern is an aggregation pattern or a non-aggregation pattern.

In the embodiment, actually, the above discrimination can be simultaneously performed with respect to eight reaction vessels 1a arranged one in each row of the microplate 1.

Figure 8A:
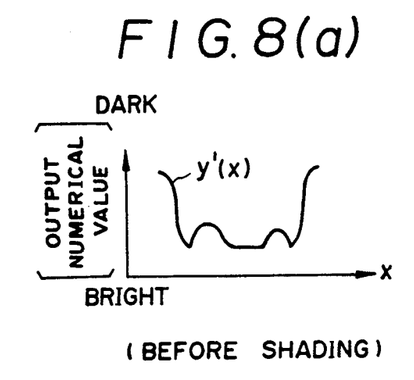
Figure 8B:
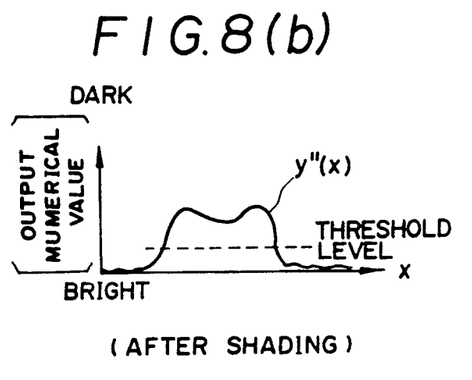

As described above, according to the embodiment, the empty plate data is previously obtained and, after that, the aggregation data is fetched and the arithmetic operations mentioned above are executed for the aggregation data and the empty plate data and the shading of the data is performed. The aggregation pattern is judged on the basis of the data of only the aggregation images as data after shading. Therefore, the discrimination is not influenced by the shapes and materials of the plate 1 and the reaction vessels 1a. It is possible to correct a variation in data due to a situation in which the aggregation image peripheral portion becomes dark due to lens aberrations of the image forming lenses 4 and the influence by the lens holder 5 and due to an uneven illumination. Thus, the aggregation patterns can be accurately discriminated. Particularly, as shown in FIG. 14 mentioned above, even in the case where the aggregation image is large and is not aggregated to the center, the data after shading as shown in FIG. 8(b) is obtained. Therefore, even if the setting of the threshold level is slightly deviated, the area data can be accurately calculated and the accurate judgement can be performed. On the other hand, since the aggregation patterns can be simultaneously discriminated with respect to eight reaction vessels 1a, high-speed judgement can be realized.

As mentioned above, even in the case of a doughnut-like aggregation image such that it is difficult hitherto to accurately discriminate the aggregation pattern by the area data, the waveform data of only the aggregation images is derived. Therefore, even if the setting of the threshold level is slightly deviated, the area data can be accurately calculated and the accurate discrimination can be performed. Thus, an excellent particle aggregation pattern discriminating method which can remarkably improve the discriminating precision and which is not conventionally derived is provided.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A method of identifying the presence or absence of an aggregation of particles which are distributed on a translucent surface, comprising the steps of:
    providing a light sensing device for sensing incident light on said translucent surface and producing an output value which represents the intensity of the incident light;
    identifying a first output value which is produced by the light sensing device when there is no light incident thereon;
    identifying a second output value which is produced by the light sensing device when, with no particles present on the translucent surface, light is directed through the translucent surface and onto the light sensing device;
    placing a reaction solution in contact with said translucent surface;
    waiting a predetermined amount of time to allow particles to be deposited on the translucent surface;
    directing light through the translucent surface on which the particles are deposited and onto the light sensing device to produce a third output value from the light sensing device;
    determining a final output value as a function of said first, second and third output values; and
    determining whether the final output value represents the presence or absence of the aggregation of particles distributed on the translucent surface.

2. The method according to claim 1, wherein said step of determining said final output value includes the further steps of:
    determining a gain value as a function of the first and second output values;
    determining a difference value which represents a difference between said first and third output values; and
    multiplying the gain value by the difference value to obtain a scaled difference value.

3. The method according to claim 2, wherein said step of determining the final output value includes the further step of determining a difference between the scaled difference value and the first output value, and defining the final output value to be said difference between the scaled difference value and the first output value.

4. The method according to claim 3, wherein said step of determining the gain value includes the steps of determining a difference between the first and second output values, and dividing a predetermined value by said difference between the first and second output values.

5. A method of discriminating a particle aggregation pattern wherein a plate for use in aggregation reaction examinations and having a plurality of reaction vessels is provided, said method comprising the steps of:
    storing dark output data into a memory from a one-dimensional photosensitive device when no light enters said photosensitive device;
    uniformly illuminating a bottom surface of a reaction vessel by a light emitting device arranged on one side of the plate;
    receiving transmitted light through an image forming lens of the one-dimensional photosensitive device arranged on the other side of the plate;
    storing empty plate data representing an empty state of the reaction vessel into the memory;
    placing a reaction solution into the reaction vessel;

waiting a predetermined amount of time after placing the reaction solution into the reaction vessel to permit precipitation of particles, and deposit thereof on the bottom surface;

reading light reception data from the one-dimensional photosensitive device which represents a precipitated state of the reaction vessel;

processing the light reception data to form precipitated plate data;

calculating aggregation image data by executing arithmetic operations based on said dark output data, said empty plate data and said precipitated plate data; and discriminating said particle aggregation pattern based on said aggregation image data.

6. The method as claimed in claim 5 wherein the step of calculating aggregation image data by executing arithmetic operations further includes the steps of:

calculating a first difference value by subtracting said precipitated plate data from said dark output data;

calculating a scaled difference value by multiplying said first difference value by a gain value; and defining said aggregation image data to be the difference between said dark output value and said scaled difference value.

7. The method as claimed in claim 6 wherein said gain value is determined by the steps of calculating a second difference value by subtracting said empty plate data from said dark output data; and dividing a predetermined value by said second difference value.

8. The method as claimed in claim 7 wherein said predetermined value is 255.

* * * * *